US007127401B2

(12) United States Patent
Miller

(10) Patent No.: US 7,127,401 B2
(45) Date of Patent: Oct. 24, 2006

(54) REMOTE CONTROL OF A MEDICAL DEVICE USING SPEECH RECOGNITION AND FOOT CONTROLS

(75) Inventor: Steven C. Miller, Pewaukee, WI (US)

(73) Assignee: GE Medical Systems Global Technology Company, LLC, Waukesha, WI (US)

( * ) Notice: Subject to any disclaimer, the term of this patent is extended or adjusted under 35 U.S.C. 154(b) by 461 days.

(21) Appl. No.: 09/681,266

(22) Filed: Mar. 12, 2001

(65) Prior Publication Data
US 2002/0128846 A1 Sep. 12, 2002

(51) Int. Cl.
G10L 21/00 (2006.01)
A61B 8/00 (2006.01)

(52) U.S. Cl. .................. 704/275; 704/270; 600/437

(58) Field of Classification Search ............. 704/275, 704/270.1, 270, 251; 381/110; 600/437
See application file for complete search history.

(56) References Cited

U.S. PATENT DOCUMENTS

| 4,776,016 | A | * | 10/1988 | Hansen | 704/275 |
|---|---|---|---|---|---|
| 5,544,654 | A | * | 8/1996 | Murphy et al. | 600/443 |
| 5,553,620 | A | | 9/1996 | Snider | |
| 5,853,367 | A | | 12/1998 | Chalek | |
| 5,867,817 | A | * | 2/1999 | Catallo et al. | 704/255 |
| 5,970,457 | A | | 10/1999 | Brant | |
| 5,971,923 | A | | 10/1999 | Finger | |
| 5,974,384 | A | * | 10/1999 | Yasuda | 704/275 |
| 6,032,120 | A | | 2/2000 | Rock | |
| 6,129,671 | A | | 10/2000 | Hastings | |
| 6,157,853 | A | * | 12/2000 | Blume et al. | 600/426 |
| 6,159,150 | A | | 12/2000 | Yale | |
| 6,171,244 | B1 | | 1/2001 | Finger | |
| 6,192,339 | B1 | * | 2/2001 | Cox | 704/275 |
| 6,210,333 | B1 | | 4/2001 | Gardner | |
| 6,212,541 | B1 | * | 4/2001 | McAuliffe et al. | 718/100 |
| 6,233,559 | B1 | * | 5/2001 | Balakrishnan | 704/275 |
| 6,238,344 | B1 | | 5/2001 | Gamelsky | |
| 6,262,749 | B1 | | 7/2001 | Finger | |
| 6,278,975 | B1 | * | 8/2001 | Brant et al. | 704/275 |
| 6,358,204 | B1 | | 3/2002 | Finger | |
| 6,371,121 | B1 | * | 4/2002 | Faries et al. | 128/849 |
| 6,393,304 | B1 | * | 5/2002 | Meche | 455/563 |
| 6,413,218 | B1 | | 7/2002 | Allison | |
| 6,417,857 | B1 | | 7/2002 | Finger et al. | |
| 6,423,002 | B1 | | 7/2002 | Hossack | |
| 6,477,498 | B1 | * | 11/2002 | Gortz et al. | 704/275 |
| 6,480,186 | B1 | | 11/2002 | McCabe | |
| 6,490,684 | B1 | | 12/2002 | Fenstemaker | |

(Continued)

*Primary Examiner*—Susan McFadden
*Assistant Examiner*—James S. Wozniak
(74) *Attorney, Agent, or Firm*—McAndrews, Held & Malloy, Ltd.; Peter J. Vogel; Michael A. Dellapenna

(57) ABSTRACT

A system and method for controlling a medical device is provided such as a medical imaging device. The preferred embodiment of the present invention receives a verbal command for assigning a function of a medical imaging device from an operator. An additional verbal command from the operator assigns an input device to control the function of the selected medical imaging device. A system control and speech recognition processor then assigns the function specified by the verbal command to the input device selected by the additional verbal command. After the function of the medical device is assigned to the input device, the operator may control the selected function of the medical device with the selected input device. The system and method provides for the unobtrusive and hands-free control of discreet and continuous functions of a medical imaging device.

20 Claims, 3 Drawing Sheets

U.S. PATENT DOCUMENTS 6,514,201 B1 * 2/2003 Greenberg .................. 600/437
6,591,239 B1 * 7/2003 McCall et al. .............. 704/275
6,642,836 B1 * 11/2003 Wang et al. ................ 704/275
6,646,541 B1 * 11/2003 Wang et al. ................ 340/3.54
2002/0190946 A1 * 12/2002 Metzger ..................... 345/156

* cited by examiner

REMOTE CONTROL OF A MEDICAL DEVICE USING SPEECH RECOGNITION AND FOOT CONTROLS

BACKGROUND OF THE INVENTION

The present invention generally relates to a system and method for controlling a medical device. More particularly, the present invention relates to a system and method for controlling a medical imaging system using a speech recognition and foot-controlled system.

Medical imaging systems are being used for a growing number of applications in the field of medicine. Medical imaging systems are typically used for diagnosis as well as for monitoring purposes during surgery. One type of medical imaging system commonly used during surgery is an ultrasound imaging system. Typical ultrasound systems operate by transmitting ultrasonic sound waves into a patient's body using a transducer. The transducer is typically a device placed on the patient's body over the area to be imaged that is capable of sending and receiving ultrasonic sound waves. The ultrasonic sound waves sent by the transducer are reflected by the patient's internal bodily structures. The reflected ultrasonic sound waves transmitted into the patient's body are then received by the transducer and processed to display a visual representation of the patient's internal bodily structures to the surgeon.

The received ultrasonic sound waves are typically processed by an ultrasonic imaging system and displayed in real time on a console for viewing by the examining physician. Typically, the console includes a control console as well as a viewing screen on which ultrasonic images are displayed. The control console typically includes a number of control devices. The control devices are typically manual controls such as dials, switches, knobs, or joysticks, for example, that may be used to manipulate the ultrasonic image displayed on the viewing screen. For example, the control devices may be used to control the resolution, magnification, viewing area, or orientation of the ultrasonic image. In typical ultrasound imaging systems, the ultrasonic images may only be adjusted or manipulated solely by the control devices.

Typically, the control console itself may be fairly large and may take up a substantial amount of space in an operating room. However, during surgery, the space around the surgeon may often be very limited. For example, multiple trays containing operating instruments, as well as other medical devices and support personnel may need to be near the surgeon to assist the surgeon during surgery. Therefore, there typically is not free space near the surgeon for the ultrasound imaging system and console during surgery. Consequently, the ultrasound imaging system and console may out of necessity need to be positioned up to several feet away from the surgeon and out of the immediate reach of the surgeon.

Typically when the console is positioned out of reach of the surgeon, the surgeon may be unable to use the control devices to manipulate the ultrasonic images during surgery. Because the surgeon is unable to manipulate the ultrasonic images during surgery, the surgery may become complicated by limiting the adjustability of the ultrasonic image. If the surgeon must adjust the ultrasonic image, the surgeon may have to continually physically walk over to the console and then adjust the properties of the image using the control devices. Requiring the surgeon to continually walk over to the control devices to adjust the ultrasonic image may be time consuming, inefficient, or impractical if the surgery requires that the surgeon continually monitor the patient.

Thus, typical ultrasonic imaging systems operable solely by control devices may be undesirable or inefficient for use by surgeons in situations where the available space around the surgeon is limited.

Even if the ultrasound imaging system and console are able to be positioned within reach of the surgeon, a number of drawbacks still exist in typical systems operable solely by console controls. For example, the surgeon's hands may be in use or too busy during the surgery to manually operate the control devices. Thus, while the surgeon may be able to reach the control devices, in practicality, the surgeon is still unable to use them. Even if the surgeon is able to operate the control devices during surgery, a number of drawbacks exist. For example, during surgery, the surgeon typically wears latex surgical gloves. The surgeon's gloves may often become covered with blood or other materials during surgery. Handling the control devices with soiled gloves may contaminate the control devices with unsterile materials, which may not present optimal sterile conditions. Thus, the control devices may have to be sterilized before, during, and after each surgery since the surgeon typically touches the control devices frequently during operation. Therefore, the control devices typically must to be made of materials that may be handled in a sterile environment.

Additionally, even sterilized control devices may be difficult to operate by a surgeon. After, the surgeon's gloves become covered with blood or other materials during surgery, the gloves may become slippery. Therefore, operation of the control devices by hand may become difficult after the surgeon's gloves become soiled. Thus, adjusting the control devices by hand in a sterile surgical environment may not be the most practical and efficient method of adjusting an ultrasonic image.

One method used to reduce some of the drawbacks associated with the limited amount of free space around a surgeon during surgery is the use of a remote control system. A remote control system is typically a compact hand-held unit including controls such as switches, dials, or joysticks, for example. Remote controls may be operable by either one or two hands. The remote control system may communicate with the medical imaging system by either a wireless transmission system or by a wire-based transmission system. The compact remote control system may be used to operate the functionality typically operated by the control devices and typically does not require that the control devices be within reach of the surgeon. Thus, the compact size of the remote control takes up less free space than the console controls.

However, remote control systems may also suffer from some significant drawbacks. For example, while the space required for the remote control system is typically less than the space required for the entire medical imaging system or console controls, some space is still required. Thus, in situations where there is very little or no free space around the surgeon, even remote control systems may still not be a viable alternative. Furthermore, remote controls systems still may present the same drawbacks that console controls exhibit with regard to sterilization and ease of use as discussed above. Additionally, the controls on the remote control system may actually be smaller than the control devices on the console to save space and thus the remote control system may be more difficult for a surgeon to manipulate, especially with soiled gloves.

One method used to reduce some of the drawbacks associated with medical imaging systems operable by control devices or remote control systems is the use of a foot-controlled console. Foot-controlled consoles are typically comprised of at least one foot-input device such as pedals, switches, or joystick-type devices for example, that may be operated by the surgeon's foot. In the medical imaging system field, such foot-controlled consoles may be used to control the functions typically controlled by the control devices of the medical imaging system.

Typically, the foot-controlled console may be placed on the floor near the surgeon's feet where operation room space is typically available. Thus, the surgeon may still control the functionality of the control console of the medical imaging system, via the foot-controlled console, even though the control console may be positioned out of reach of the surgeon. That is, although the foot-controlled console may not occupy any space in the limited operating space directly around the surgeon's hands and torso, the foot-controlled console allows for hands-free operation of the functionality of the medical imaging system's control devices by the surgeon during surgery. Hands-free operation may reduce the problems associated with manually operating control devices or remote controls as discussed above.

However, the typical foot-controlled console system may still suffer from some significant drawbacks. One drawback that may occur in typical foot-controlled consoles is reduced functionality. That is, the foot-controlled console may lack much of the functionality that the control console has. The reduced functionality of foot-controlled consoles may occur for a number of reasons. One reason a foot-controlled console may lack some of the functionality that the control console has is that there is limited space available on a foot-controlled console. Typical control consoles may include a large number of control devices for a wide variety of features of the medical imaging system. Therefore, in order to accommodate control of each feature of the medical imaging system, a large number of foot-input devices may need to be placed on the foot-controlled console. Because the surgeon's feet are typically larger and less agile than the surgeon's hands, the foot-input devices on the foot-controlled console typically may be larger and spaced further apart than the corresponding control devices on a typical control console. Thus, if the number of control devices on the medical imaging system console is high, the corresponding foot-controlled console may become too large and inefficient to use in practice. Therefore, in order to keep the foot-controlled console compact enough for efficient use, a limited number of foot-input devices, typically less than the number of control devices, may have to be placed on the foot-controlled console limiting the functionality of the foot-controlled console.

In applications outside of the medical imaging field, control and functionality of various systems have been provided by voice-controlled systems. For example, the use of voice-controlled systems has been adopted in fields such as computer science to facilitate hands-free operation of personal computers. Typical voice-controlled systems utilize a microphone and a speech recognition system. Typically, an operator speaks a verbal command into the microphone, and the command is then transmitted to the speech recognition system. The speech recognition system is typically pre-programmed to recognize the command. After recognizing the verbal command, the speech recognition system typically sends a signal to the device being controlled to perform the operator's command. Thus, speech recognition systems allow an operator to control a device in a completely hands-free manner. However, voice-controlled systems may suffer from some significant drawbacks. These drawbacks may make the use of typical voice-controlled systems in the medical imaging field very difficult.

For example, one drawback that may be present in speech recognition systems is the inability to make fine adjustments to continuous controls such as a joystick, trackball, or dial, for example. That is, verbal commands typically are not able to provide small continuous movements of controls, which may often be required of medical imaging systems. Therefore, the use of speech recognition systems may not be optimal for surgical applications because of their inability to perform fine adjustment. Another drawback is that typical speech recognition systems may react slowly to commands. Therefore, in a real-time environment such as during surgery, a significant lag time between a command and execution of the command may complicate the surgery or hinder progress. Furthermore, speech recognition systems are typically sensitive to external noise. That is, speech recognition systems typically need to be operated in a quiet environment to function properly. Noises other than the operator's voice, such as other voices or noise from other devices in surgery for example, may cause the speech recognition system to register false commands.

Thus, a need exists for a medical imaging control system that may be efficiently used in the limited operating area of a surgeon. A need further exists for a medical imaging control system that may be efficiently used in the limited operating area of a surgeon while maintaining all of the functionality available to console controls. Additionally, a need exists for a medical imaging control system that allows for the efficient control of continuous controls such as joysticks, trackballs, or dials, for example, during surgery.

SUMMARY OF THE INVENTION

The preferred embodiment of the present invention provides a system and method for controlling a medical imaging system using a speech recognition and foot-controlled system. A preferred embodiment of the present invention includes a microphone for receiving and transmitting verbal commands from a surgeon to a system control and speech recognition processor. The present invention also preferably includes a foot-input console connected to the system control and speech recognition processor. To operate the medical imaging system using the speech recognition and foot-controlled system, the surgeon preferably speaks a first verbal command into the microphone. The first verbal command selects a specific function available on the medical imaging system. The surgeon then preferably speaks a second verbal command assigning a foot-input device located on the foot-input console control over the functionality specified in the first verbal command. Once the function specified in the first verbal command is successfully assigned to the foot-input device specified in the second verbal command, the surgeon may then control the function of the medical imaging device in a hand-free manner via the foot during surgery.

DETAILED DESCRIPTION

Figure 1:
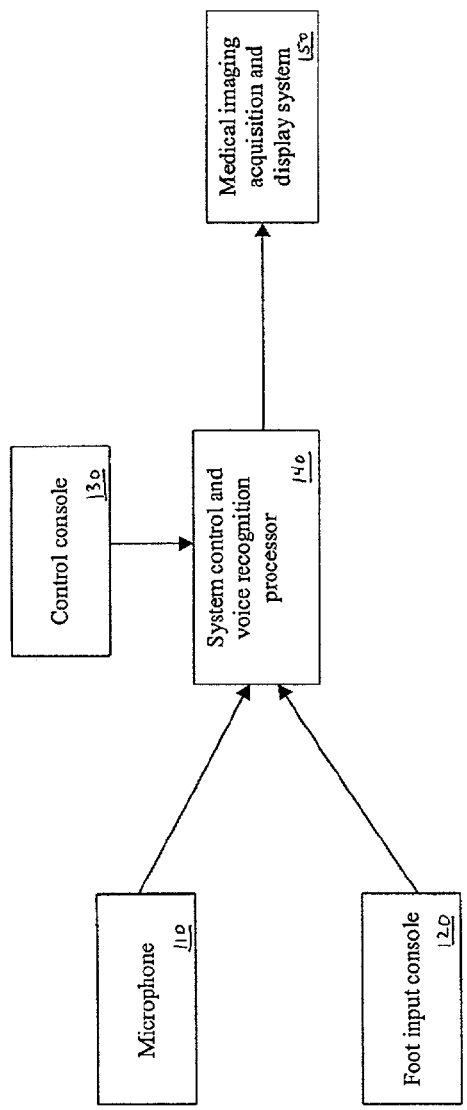
FIG. 1 illustrates a block diagram of a voice activated, foot-controlled medical imaging control system according to a preferred embodiment of the present invention.

FIG. 1 illustrates a block diagram of a voice activated, foot-controlled medical imaging control system 100 according to a preferred embodiment of the present invention. The medical imaging control system 100 includes a microphone 110, a foot input console 120, a control console 130, a system control and speech recognition processor 140, and a medical imaging acquisition and display system 150.

The microphone 110 is connected to the system control and speech recognition processor 140. The foot input console 120 is also connected to the system control and speech recognition processor 140. The control console 130 is also connected to the system control and speech recognition processor 140. The system control and speech recognition processor 140 is connected to the medical imaging acquisition and display system 150.

In operation, a surgeon's voice commands are sent to the system control and speech recognition processor 140 via the microphone 110 to assign the functionality of the control console 130 to the foot-input console 120. Preferably, the microphone 110 of the medical imaging control system 100 is attached to a headset worn by the surgeon during surgery. The microphone 110 may be connected to the system control and speech recognition processor 140 by either a wireless transmission system or by a wire-based transmission system. The foot-input console 120 of the medical imaging control system 100 is preferably located on the floor of the operating room within reach of the surgeon's foot. The foot-input console 120 preferably includes at least one foot-input device such as a pedal or switch, for example. The foot-input console 120 may be connected to the system control and speech recognition processor 140 by either a wireless transmission system or by a wire-based transmission system. The control console 130 is typically located in the operating room but out of reach of the surgeon because of the limited space around the surgeon. The control console 130 preferably includes at least one control device such as a knob or dial, for example. The control devices on the control console 130 are typically used by the surgeon to adjust the properties of an ultrasound image or perform an imaging function. For example, the control devices may be used to print or freeze the image, change the focal zone of the image, adjust the contrast or resolution of the image, or adjust the orientation of the image. The medical imaging acquisition and display system 150 typically includes a system for generating and displaying medical images for the surgeon. The medical images are typically displayed on a LCD screen or monitor located in the operating room.

Although the medical imaging control system 100 is described below with reference to ultrasonic images, the present invention may be used in conjunction with any type of medical images such as MRI or CT scan images for example. The medical imaging control system 100 described below may be adapted with minimal modifications for use with any type of medical imaging by methods know to those skilled in the art.

In operation of the preferred embodiment where the medical imaging control system 100 is used, the surgeon activates the medical imaging control system 100 through the use of two verbal commands. The first verbal command preferably selects the specific functionality of the control console 130 to be assigned to the foot-controlled console 120. The second verbal command then preferably selects the specific foot-input device on the foot-controlled console 120 to control the selected functionality. After giving the two verbal commands, the surgeon may then control the functionality of the control console 130 with the foot-controlled console 120.

For example, the medical imaging acquisition and display system 150 generates and displays medical images of the patient to the surgeon. During the surgery, the surgeon may wish to adjust the properties of an image to get a different perspective of the patient's internal structures or to zoom in on a point of interest for example. However, as discussed above with regard to the background section, because of space limitations or because the surgeon may be using both hands, the console control 130 of the medical imaging system may be out of reach or impractical to use. Thus, in order to adjust the ultrasound images hands-free during surgery using the medical imaging control system 100 the surgeon speaks a first verbal command into the microphone 110. The first verbal command spoken by the surgeon into the microphone 110 preferably is the name of a specific function performed by the medical imaging system such as "zoom" for example. The microphone 110 then transmits the signal of the first verbal command to the system control and speech recognition processor 140. The system control and speech recognition processor 140 then compares the signal of the first verbal command to a number of pre-programmed signals stored in a database look-up table in the system control and speech recognition processor 140. Some signals stored in the database look-up table correspond to a specific function of the medical imaging system. If the signal of the first verbal command matches one of the stored signals, the functionality spoken in the first verbal command is selected.

The surgeon then speaks a second verbal command into the microphone 110. The second verbal command spoken by the surgeon into the microphone 110 is the name of a specific foot-input device on the foot input console 120 such as "pedal one" for example. The microphone 110 then transmits the signal of the second verbal command to the system control and speech recognition processor 140. The system control and speech recognition processor 140 compares the signal of the second verbal command to a number of pre-programmed signals stored in the database look-up table. Some signals stored in the system control and speech recognition processor 140 correspond to specific foot-input devices on the foot-controlled console. If the signal of the second verbal command matches one of the stored signals, the system control and speech recognition processor 140 assigns the foot-input device spoken in the second verbal command to the functionality spoken in the first verbal command. Once the system control and speech recognition processor 140 assigns the control device functionality to the foot-input device, the surgeon may use the foot-input device to adjust the specified property of the ultrasound image.

Additionally, during the surgery, the surgeon may either reassign the foot-input device to the functionality of another control device, or assign the functionality of multiple control devices to multiple foot input devices by repeating the procedure described above. While the present invention has been discussed with reference to a preferred embodiment of controlling a medical imaging system, the present invention may be used to control any medical device in a hands-free manner.

Figure 2:
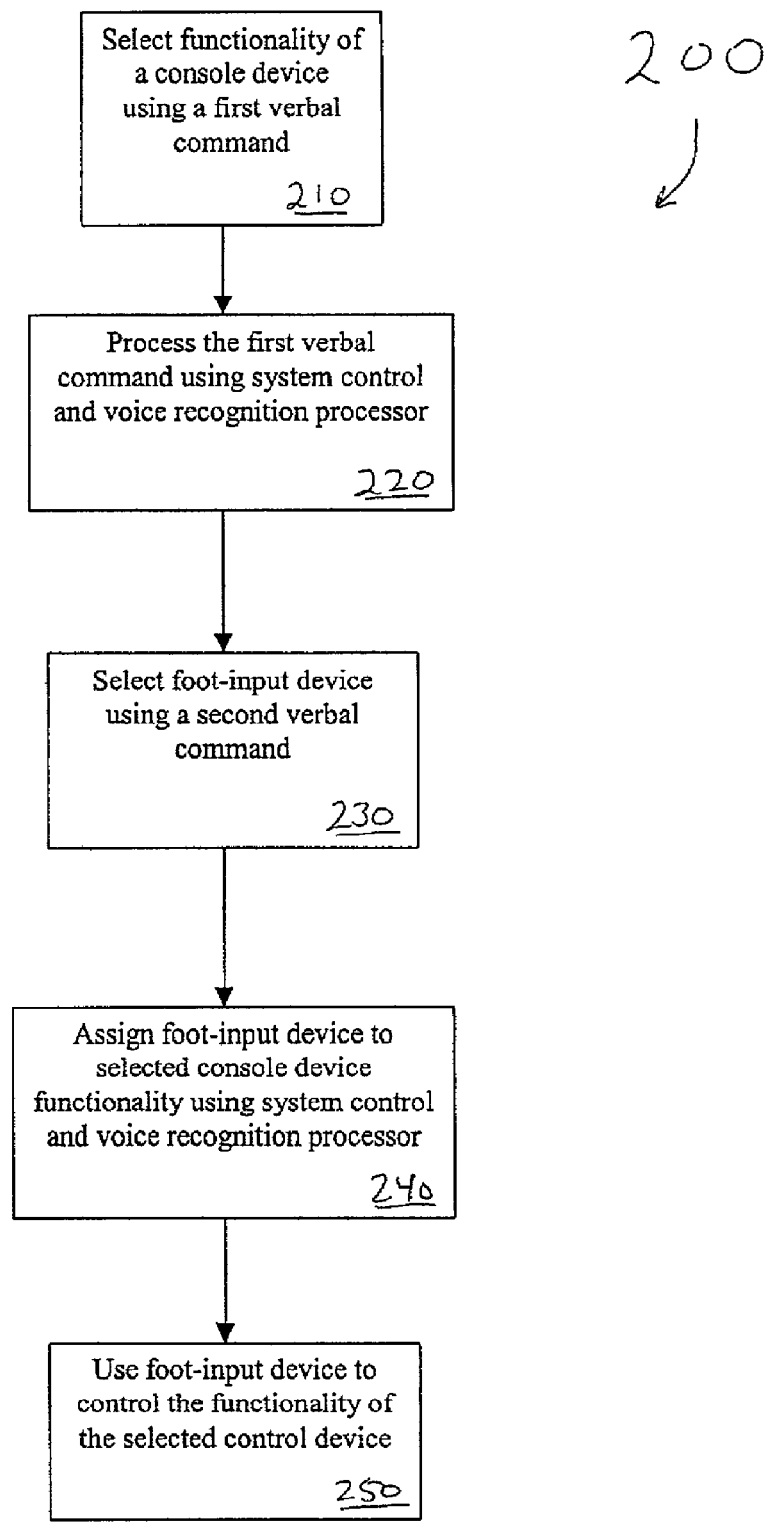
FIG. 2 illustrates a flow chart of the voice activated, foot-controlled medical imaging control system according to a preferred embodiment of the present invention.

FIG. 2 illustrates a flow chart 200 of the use of the medical imaging control system of FIG. 1 according to a preferred embodiment of the present invention. First, at step 210, the surgeon selects the functionality of a control device by speaking a first verbal command into a microphone 110. The microphone 110 then transmits the signal of the first verbal command to the system control and speech recognition processor 140. Then, at step 220, the system control and speech recognition processor 140 processes the first verbal command by comparing the signal of the first verbal command to a number of pre-programmed signals stored in the system control and speech recognition processor 140. If the signal of the first verbal command matches one of the stored signals, the functionality spoken in the first verbal command is selected. Next, at step 230, the surgeon selects the foot-input device to control the control device selected at step 210, by speaking a second verbal command into the microphone 110. The microphone 110 then transmits the signal of the second verbal command to the system control and speech recognition processor 140. At step 240, the system control and speech recognition processor 140 then assigns the foot-input device selected at step 230 to the control device selected at step 210 by comparing the signal of the second verbal command to a number of pre-programmed signals stored in the system control and speech recognition processor 140. If the signal of the second verbal command matches one of the stored signals, the system control and speech recognition processor 140 assigns the foot-input device spoken in the second verbal command to the functionality spoken in the first verbal command. Finally, at step 250, once the control device functionality is successfully assigned to the foot-input device, the surgeon may control the functionality selected at step 210 with the foot-input device selected at step 230.

Figure 3:
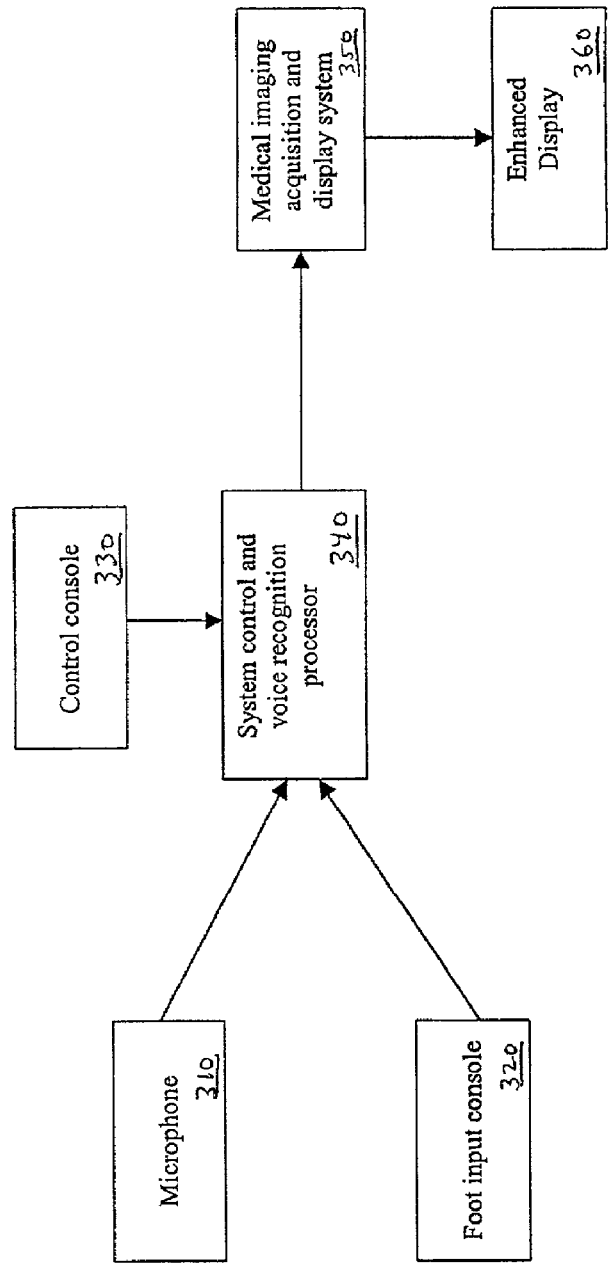
FIG. 3 illustrates a block diagram of an alternative embodiment of a voice activated, foot-controlled medical imaging control system.

FIG. 3 illustrates a block diagram of an alternative embodiment 300 of the medical imaging control system 100 of FIG. 1. The alternative embodiment 300 includes a microphone 310, a foot input console 320, control console 330, a system control and speech recognition processor 340, and a medical imaging acquisition and display system 350 similarly to FIG. 1 above. Additionally, the alternative embodiment 300 includes an enhanced display 360.

As similarly described above with regard to FIG. 1, the microphone 310, the foot-input console 320, and the control console 330 are all connected to the system control and speech recognition processor 340. The system control and speech recognition processor 340 is connected to the medical imaging acquisition and display system 350. The enhanced display 360 is connected to medical imaging acquisition and display system 350.

In the alternative embodiment 300, the microphone 310, the foot-input console 320, the control console 330, the system control and speech recognition processor 340, and the medical imaging acquisition and display system 350, function in substantially the same manner as described above with regard to FIG. 1. However, the enhanced display 360 of the alternative embodiment 300 includes extra functionality not present in the medical imaging acquisition and display system 150 of FIG. 1. The enhanced display 360 is preferably a LCD screen or monitor placed in clear view of the surgeon during surgery. In addition to displaying the medical images to the surgeon during surgery, the enhanced display 360 may also display additional information to the surgeon. For example, the additional information displayed to the surgeon may include which functionality is currently assigned to each foot-input device, or the current state of the medical imaging control system during assignment of functionality to the foot-input device. The additional information may be displayed in the form of text, icons, or preferably drop-down menus, for example.

In operation of the alternative embodiment 300, the surgeon speaks the first verbal command into the microphone 310 as similarly described above with reference to FIG. 1. However, after the first verbal command is received and recognized by the system control and speech recognition processor 340, a drop-down menu preferably appears on the enhanced display 360. Once the functionality has been selected, the drop-down menu may either appear over the medial image being displayed or next to the medical image on the enhanced display 360. The top of the drop-down menu then preferably lists the name of functionality specified in the first verbal command. Below the name of the selected functionality listed in the drop-down menu is preferably the list of names of the assignable foot-input devices available for assignment on the foot-input console 320. Thus, the surgeon is provided with a visual confirmation that the first verbal command was successfully recognized by the system control processor and speech recognition processor 340 when the drop-down menu appears on the enhanced display. Furthermore, the surgeon is then presented with a list of available foot-input devices to choose from.

Next, the surgeon speaks the second verbal command into the microphone 310 as similarly described with regard to FIG. 1. The second verbal command then assigns the commanded foot-input device specified in the second verbal command to the specified functionality of the first verbal command in substantially the same manner as described above in FIG. 1. Additionally, after the foot-input device is assigned functionality, the functionality assigned to the foot-input device is preferably continually displayed on the enhanced display 360. Displaying the assignment information on the enhanced display 360 allows the surgeon to review which foot-input devices have been assigned functionality, thus making the use of the medical imaging control system easier and more efficient.

In a second alternative embodiment of the present invention, the enhanced display 360 described above in FIG. 3 may be a head-mounted display instead of a LCD panel or monitor. A head-mounted display is typically a device worn on the operator's head which projects an image viewable by the operator. The image projected by the head-mounted display may either be projected directly into the operator's eye or reflected into the operator's eye using a mirror. The head-mounted display may be either a monocular head-mounted display, or a see-through head-mounted display. In either case the drop-down menu alone or preferably the medical image and drop-down menu may be displayed to the surgeon via the head-mounted display. The head-mounted display may allow the surgeon to have the patient, the medical images, and the medical imaging system information, in the surgeon's field-of-view during the surgery. Having all of this visual information in front of the surgeon may reduce the amount of head movements required by the surgeon to access all of this information. Reducing the number of head movements may increase the ease, speed, and efficiency of the surgery.

In a third alternative embodiment of the present invention, the order of verbal commands may be reversed. That is, the first verbal command spoken by the surgeon selects the foot-input device to be assigned a function. Consequently, the second verbal command spoken by the operator then selects the functionality of the medical imaging system to be assigned to the foot-input device in the first verbal command. The rest of the medical imaging control system in the third alternative embodiment functions in substantially the same manner as discussed above with regard to FIG. 1.

While the invention has been described with reference to a preferred embodiment, it will be understood by those skilled in the art that various changes may be made and equivalents may be substituted without departing from the scope of the invention. In addition, many modifications may be made to adapt a particular situation or material to the teachings of the invention without departing from its scope. Therefore, it is intended that the invention not be limited to the particular embodiment disclosed, but that the invention will include all embodiments falling within the scope of the appended claims.

The invention claimed is:

1. A system for controlling a function of a medical imaging device, said system including:
   a microphone for receiving a plurality of verbal commands from an operator;
   a system control and speech recognition processor for receiving a first verbal command from said microphone for selecting a function and receiving a second verbal command from said microphone for assigning said function to one of a plurality of foot input devices, said foot input device controlling the assigned function when activated by a user; and
   a display for displaying visual confirmation that said first verbal command was successfully recognized by said system control and speech recognition processor and for displaying visual confirmation that said second verbal command was successfully recognized by said system control and speech recognition processor, wherein the display also displays a current medical imaging device function that is assigned to one of the plurality of foot input devices.

2. The system of claim 1 wherein said visual confirmation is performed by use of a drop-down menu.

3. The system of claim 1 wherein said system control and speech recognition processor is programmed to recognize a verbal command as a predetermined verbal command.

4. The system of claim 1 wherein said system control and speech recognition processor is programmed to recognize a predetermined function.

5. The system of claim 1 wherein said medical imaging device is an ultrasonic medical imaging device.

6. A system for controlling a function of a medical imaging device, said system including:
   a microphone for receiving a plurality of verbal commands from an operator;
   a system control and speech recognition processor for receiving a first verbal command for selecting a function and receiving a second verbal command for assigning said function to one of a plurality of foot input devices, said foot input device controlling the assigned function when activated by a user; and
   a display for continuously displaying a current function assigned to each foot input device, wherein the current function is a medical imaging device function.

7. The system of claim 6 wherein said display displays medical images.

8. The system of claim 6 wherein said system control and speech recognition processor is programmed to recognize a predetermined verbal command.

9. The system of claim 6 wherein said system control and speech recognition processor is programmed to recognize a predetermined function.

10. The system of claim 6 wherein said medical imaging device is an ultrasonic medical imaging device.

11. A system for assigning a function of a medical imaging device to an input device, said system including:
   a system control and speech recognition processor for receiving a first verbal command from an operator for selecting a function and receiving a second verbal command from an operator for assigning said function to one of a plurality of foot input devices, said foot input device controlling the assigned function when activated by a user; and
   a display for displaying visual confirmation that said first verbal command was successfully recognized by said system control and speech recognition processor and for displaying visual confirmation that said second verbal command was successfully recognized by said system control and speech recognition processor, wherein the display also displays a current medical imaging device function that is assigned to one of the plurality of foot input devices.

12. The system of claim 11 further including a microphone for receiving said verbal commands from said operator.

13. The system of claim 11 wherein said visual confirmation is performed by use of a drop-down menu.

14. The system of claim 11 wherein said system control and speech recognition processor is programmed to recognize a predetermined verbal command.

15. The system of claim 11 wherein said system control and speech recognition processor is programmed to recognize a predetermined function.

16. The system of claim 11 wherein said medical imaging device is an ultrasonic medical imaging device.

17. A method for controlling a function of a medical imaging device, said method including the steps of:
   receiving a first verbal command from an operator;
   selecting a function in response to said first verbal command;
   displaying visual confirmation that said first verbal command was successfully recognized;
   receiving a second verbal command from an operator;
   assigning said function to one of a plurality of foot input devices in response to said second verbal command;
   displaying visual confirmation that said second verbal command was successfully recognized;
   displaying a current medical imaging function assigned to one of the plurality of foot input devices; and
   controlling said function assigned to said foot input device when said input device is activated by an operator.

18. The method of claim 17 wherein said verbal commands are received by a microphone.

19. A method for assigning a function of a medical imaging device to an input device, said method including the steps of:
   receiving a first verbal command for selecting a function;
   receiving a second verbal command for assigning said function to one of a plurality of foot input devices;
   assigning said function to said foot input device in response to said second verbal command;
   displaying a current function assigned to each foot input device, wherein the current function is a medical imaging device function; and
   controlling said function assigned to said foot input device in response to said verbal commands when said input device is activated by an operator.

20. The method of claim 19 wherein said verbal commands are received by a microphone.

* * * * *